US00PP30041P3

(12) United States Plant Patent
Fouillet

(10) Patent No.: US PP30,041 P3
(45) Date of Patent: Jan. 1, 2019

(54) APPLE TREE NAMED 'Y102'

(50) Latin Name: *Malus domestica*
Varietal Denomination: Y102

(71) Applicant: International Fruit Obtention (IFO) GIE, Seiches sur le Loir (FR)

(72) Inventor: Valérie Fouillet, Saint Sylvain d'Anjou (FR)

(73) Assignee: International Fruit Obtentions (IFO) GIE, Seiches sur le Loir (FR)

( * ) Notice: Subject to any disclaimer, the term of this patent is extended or adjusted under 35 U.S.C. 154(b) by 0 days.

(21) Appl. No.: 15/330,525

(22) Filed: Sep. 30, 2016

(65) Prior Publication Data

US 2018/0098470 P1 Apr. 5, 2018

(51) Int. Cl.
*A01H 5/08* (2018.01)
*A01H 6/74* (2018.01)

(52) U.S. Cl.
USPC ..... Plt./161
CPC ..... *A01H 6/7418* (2018.05); *A01H 5/08* (2013.01)

(58) Field of Classification Search
USPC ..... Plt./161
CPC ..... A01H 5/0875
See application file for complete search history.

*Primary Examiner* — Kent L Bell
(74) *Attorney, Agent, or Firm* — Michelle Bos Legal LLC

(57) ABSTRACT

'Y102' apple tree is a new variety selected for its distinctive pink and light yellow-fleshed fruit, which is well-suited for the fresh market.

5 Drawing Sheets

Latin name: *Malus domestica.*
Variety denomination: 'Y102'.

BACKGROUND OF THE VARIETY

'Y102' is a new and distinct variety of apple tree (*Malus domestica*) obtained from a controlled cross of 'Golden Delicious' (female parent, not patented) x 'SJ109' (male parent, not patented) carried out at Seiches sur le Loir, France in 2006. Seeds obtained from the cross were planted at Seiches sur le Loir, and 'Y102' was selected from the resulting seedlings for propagation and further observation. 'Y102' was first asexually propagated by grafting in 2011 at Seiches sur le Loir, and has since been observed to remain true to type over successive asexually propagated generations.

BRIEF DESCRIPTION OF THE VARIETY

'Y102' apple tree is distinguished by its fruit, which has pink flesh and is well-suited for fresh consumption. 'Y102' is distinguished from its parents as shown in Tables 1 and 2 below.

TABLE 1

Comparison of 'Y102' to 'Golden Delicious'

| Characteristic | 'Y102' | 'Golden Delicious' |
|---|---|---|
| Harvest time | 5-10 days later than 'Golden Delicious' | Mid to late September |
| Flesh Color | Pink and light yellow | White |
| Skin Color | Dark orange-yellow | Yellow |

TABLE 2

Comparison of 'Y102' to 'SJ109'

| Characteristic | 'Y102' | 'SJ109' |
|---|---|---|
| Fruit Shape | Round | Flat-round |
| Texture | Crunchy | Mealy, soft |
| Storageability | Moderate (2 months) | Short (less than 1 month) |
| Taste | Balanced sugar/acid | Acidic |

BRIEF DESCRIPTION OF THE PHOTOGRAPHS

The accompanying photographs of the 'Y102' variety were taken in 2016 at Seiches sur le Loir, France.

DETAILED BOTANICAL DESCRIPTION OF THE VARIETY

Figure 1:
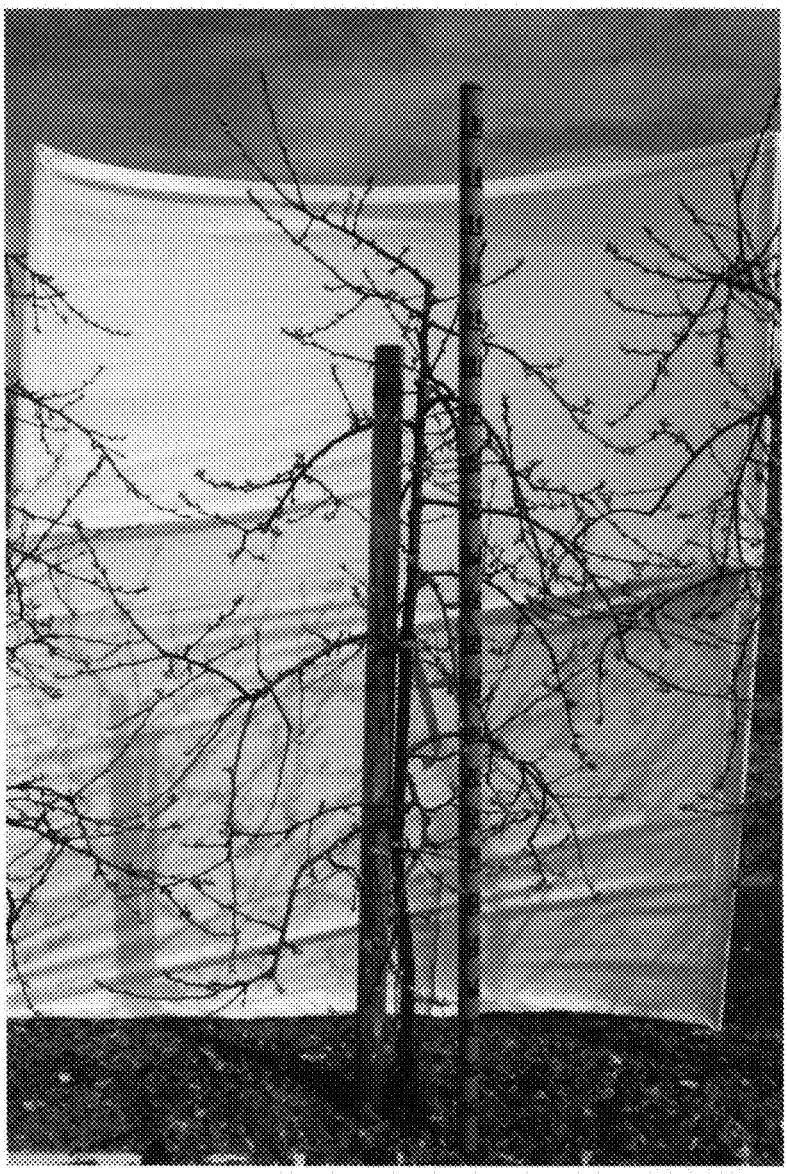
FIG. 1 is a photograph of a 'Y102' apple tree.
Figure 2:
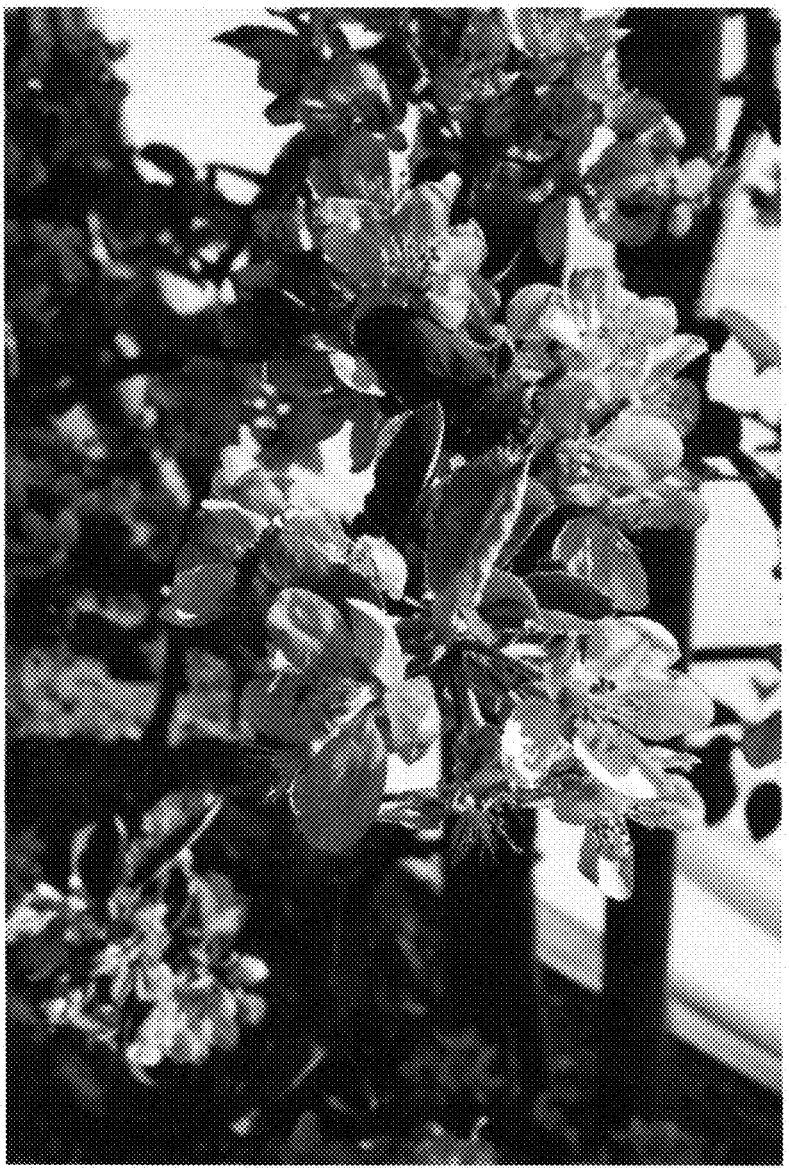
FIG. 2 is a photograph of flowers and young leaves on a 'Y102' apple tree.
Figure 3:
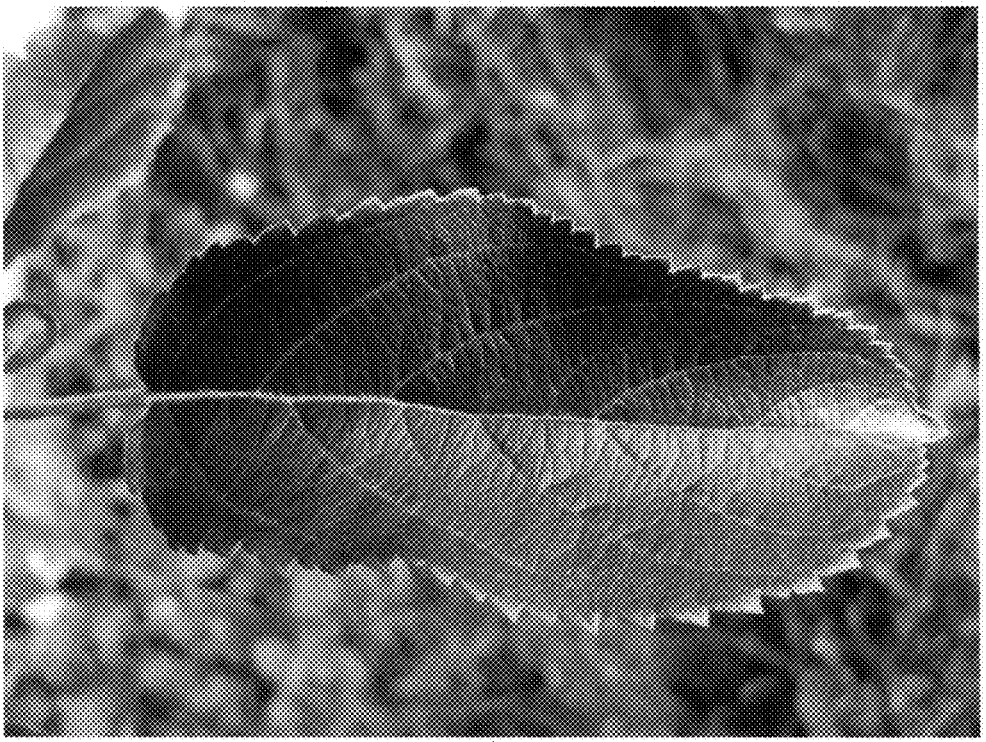
FIG. 3 is a photograph of a leaf of the 'Y102' apple tree.
Figure 4:
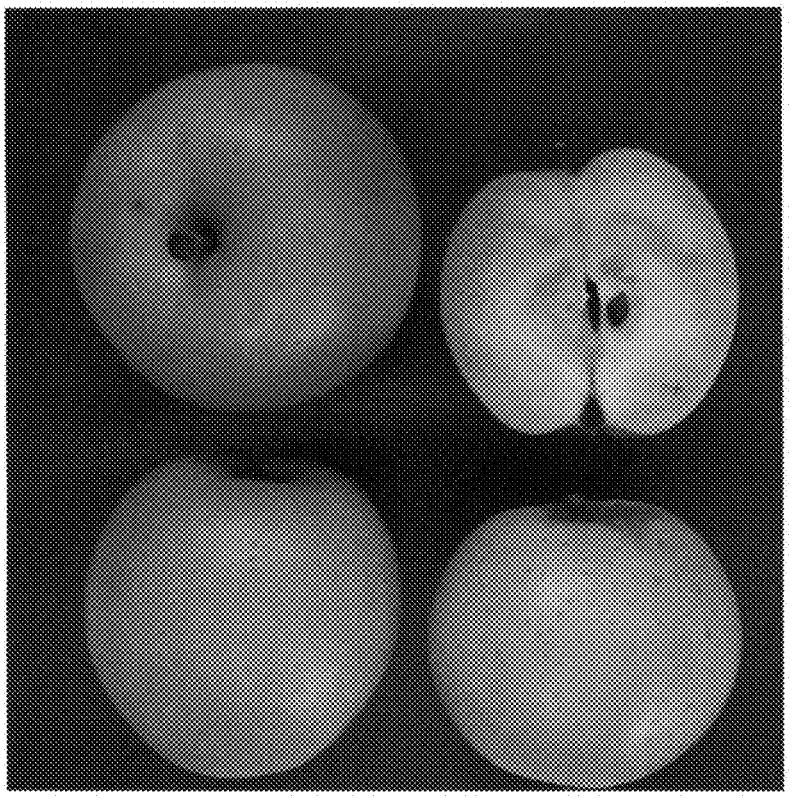
FIG. 4 is a photograph of whole and sectioned 'Y102' apples.
Figure 5:
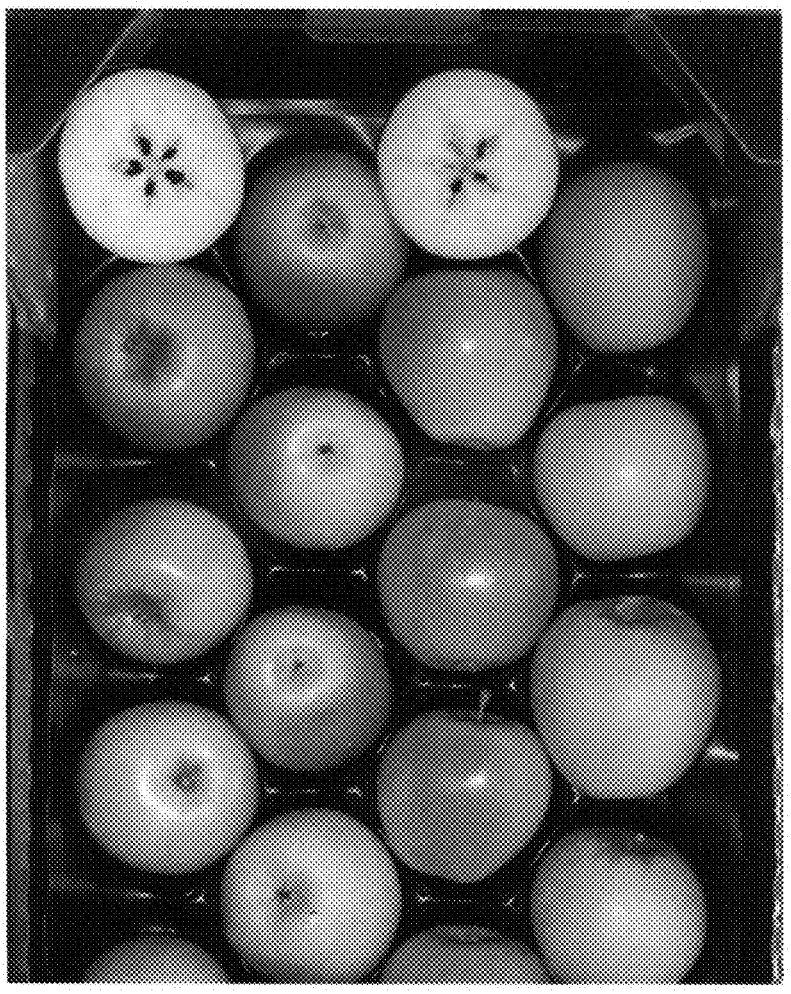
FIG. 5 is a photograph of whole and sectioned 'Y102' apples.

The following detailed botanical description is based on observations made at Seiches sur le Loir, France during the 2016 growing season (unless otherwise noted), of two year old trees grown on Pajam®2 'Cepiland' rootstock (U.S. Plant Pat. No. 7,715). All colors are described according to The Royal Horticultural Society Mini Colour Chart (2005). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:
*Vigor*.—Medium to high.
*Type*.—Ramified.
*Habit*.—Drooping.
*Height*.—Approximately 2.3 m.
*Trunk diameter* (*at* 30 *cm above the graft*).—34 mm.
*Bark texture*.—Smooth.
*Bark coloration*.—Grey N200C.

Branch (fruiting branches located at around 1 m above the graft union):
*Length*.—80 cm.
*Diameter*.—15 mm.
*Crotch angle*.—70°.
*Bark color*.—Grey N200C.
*Lenticel length*.—1.2 mm.
*Lenticel color*.—Dark orange yellow 22A.
*Number of lenticels per cm*$^2$.—6.

One year old shoot:
*Length*.—60 cm.
*Color*.—Purple brown 166A.
*Pubescence*.—Medium.
*Thickness*.—5.5 mm to 6.5 mm.
*Internode length*.—3.5 cm.
*Shoot lenticel width*.—1 mm.
*Shoot lenticel length*.—1 mm.
*Shoot lenticel color*.—Dark orange yellow 22A.
*Number of lenticels per cm*$^2$.—11.

Flower buds:
*Quantity per spur*.—5.
*Shape*.—Ellipsoid.
*Length*.—13 mm.
*Diameter*.—5 mm.
*Color*.—Light yellow brown 160B.

Flowers:
*Diameter of fully open flower*.—30 mm.
*Depth of fully open flower*.—11 mm.
*Relative position of petal margin*.—Touching.
*Number per cluster*.—5 to 7.
*Date of first bloom*.—Apr. 13, 2018 in Loire Valley, France; about 5 days before 'Golden Delicious'.
*Date of full bloom*.—Apr. 16, 2018 in Loire Valley, France; about 7 days before 'Golden Delicious'.
*Pollination requirement*.—'Gala', 'Granny Smith', 'Golden Delicious' and 'Cripps Pink' are suitable pollinators.

Petals:
*Number per flower*.—5.
*Shape*.—Elliptical.
*Length*.—18 mm.
*Width*.—12 mm.
*Apex*.—Obtuse.
*Base*.—Acute.
*Margin*.—Smooth.
*Coloration of upper surface*.—Pink Violet 75C.
*Coloration of lower surface*.—Pink Violet 77D.

Pistils:
*Length*.—11 mm.
*Color*.—Light yellow green 150B.

Stigma:
*Length*.—1 mm.
*Color*.—Light yellow brown 163B.

Style:
*Length*.—6 mm.
*Color*.—Yellow green 145C.

Ovary:
*Length*.—4 mm.
*Color*.—Yellow green 145C.

Anthers:
*Quantity*.—16 to 20.
*Length*.—2 mm.
*Presence of pollen*.—Present, abundant.
*Color of pollen*.—Light yellow 8C.

Pedicel:
*Length*.—14 mm.
*Diameter*.—1.5 mm.
*Color*.—Green 139C.

Sepals:
*Quantity*.—5.
*Length*.—6 mm.
*Width*.—3 mm.
*Color—upper surface*.—Green 138D.
*Color—lower surface*.—Green 141D.
*Shape*.—Pointed.
*Margin*.—Smooth.

Leaves:
*Shape*.—Elliptical.
*Length*.—78 mm.
*Width*.—48 mm.
*Length/width ratio*.—1.63.
*Blade margin*.—Sharply serrate.
*Apex*.—Right-angled to obtuse.
*Base shape*.—Obtuse.
*Color of upper surface*.—Dark green 136 A.
*Color of lower surface*.—Green 137C.
*Attitude in relation to shoot*.—Upwards.

Petiole:
*Length*.—27 mm.
*Diameter*.—1.4 mm.
*Coloration*.—Yellow green 145C with some purple 58A.

Fruit:
*Quantity per cluster*.—2-3.
*Diameter*.—72 mm.
*Height*.—76 mm.
*Weight*.—194 g.
*Ratio of height to width*.—1.05.
*General shape in profile*.—Globose asymmetric.
*Position of maximum diameter*.—Middle of the fruit.
*Ribbing*.—Absent or weak.
*Crowning at calyx end*.—Weak.
*Size of eye*.—Medium.
*Aperture of eye*.—Weak to moderate.
*Length of sepal*.—4 mm.
*Bloom of skin*.—Absent or weak.
*Greasiness of skin*.—Moderate.
*Amount of over color*.—Moderate to large, about 70%.
*Color of skin*.—Dark orange-yellow 22A.
*Intensity of over color*.—Medium.
*Pattern of over color*.—Only solid flush.
*Amount of russet around stalk cavity*.—Weak to moderate.
*Amount of russet on cheeks*.—Absent or weak.
*Area of russet around eye basin*.—Absent.
*Length of stalk*.—17 mm.
*Thickness of stalk*.—2.5 mm.
*Depth of stalk cavity*.—13 mm.
*Width of stalk cavity*.—23 mm.
*Depth of eye basin*.—7 mm.
*Width of eye basin*.—23 mm.

*Firmness of flesh*.—Medium to high, 7.5 kg/cm$^2$ after 3 weeks storage.
*Flesh texture*.—Fine.
*Aroma*.—Medium to high.
*Juiciness*.—Medium to high.
*Brix*.—14.5° Brix.
*Flesh coloration*.—Light red pink 38B and light yellow brown 158D.
*Stem coloration*.—Brown N199C.

Seeds:
*Quantity per fruit*.—8 to 9.
*Length*.—9 mm.
*Wedth*.—5 mm.
*Shape*.—Oval — oblong.
*Coloration*.—Dark brown 200 C.

Harvest:
*Time for harvest*.—Mid-season, 5-7 days after 'Golden Delicious'; Sep. 20, 2017 in Loire Valley, France.
*Number of picks*.—2 to 3.
*Fruit load per tree*.—High.
*Harvest yield*.—12 to 16 kg per tree ($6^{th}$ leaf trees).

Disease resistance/susceptibility: No resistance noted.
Pest resistance/susceptibility: None noted.
Market use: Fresh eating.
Eating quality: Very good.
Storageability: Medium to good at 3 to 4° C.

I claim:

1. A new and distinct apple tree as described and illustrated herein.

* * * * *